Jan. 15, 1974 A. W. FISCHER Plant Pat. 3,436
AFRICAN VIOLET PLANT
Filed Jan. 24, 1972
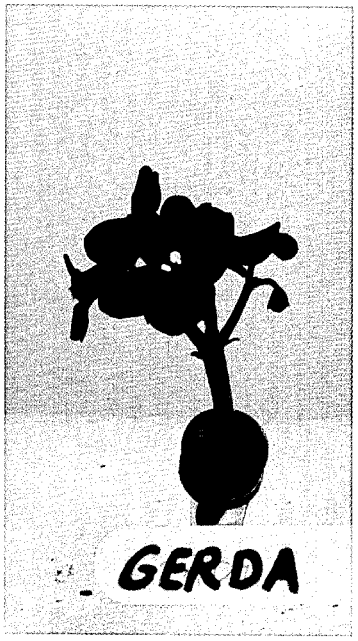
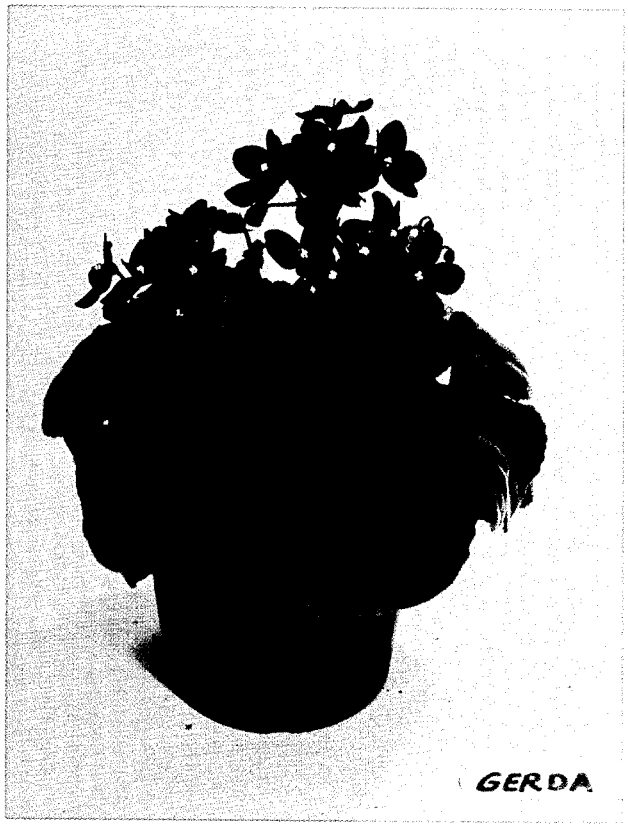

United States Patent Office

Plant Pat. 3,436

Patented Jan. 15, 1974

3,436

AFRICAN VIOLET PLANT

Arnold W. Fischer, Isernhagen, Germany, assignor to Geo. J. Ball, West Chicago, Ill.

Filed Jan. 24, 1972, Ser. No. 220,504
Int. Cl. A01h 5/00
U.S. Cl. Plt.—69 1 Claim

ABSTRACT OF THE DISCLOSURE

A new variety of African violet plant distinguished by the very deep violet color of its blossoms, which bloom recurrently the year around, its uniform and heavy flowering habit and its very abundant foliage.

BACKGROUND OF THE INVENTION

This new variety of African violet plant originated as a seedling developed by me at Isernhagen, Germany, where I have been conducting the culture and breeding of African violets for the purpose of developing improved varieties for the potted plant market. This new plant was selected for test because of the deep violet color of its blooms and the upstanding growth of the flower stalks which hold the blossoms in compact group well above the foliage. Asexual propagation of this plant under my direction and by means of leaf cuttings, at Isernhagen, Germany, demonstrated the plant to retain all of its original and distinctive characteristics from generation to generation and because of its vigorous growth and attractive display of the blooms of unusual color, this new plant was selected for propagation on a commercial scale. Commercial propagation is now being carried on at West Chicago, Ill., U.S.A., by means of leaf cuttings and division of shoots.

DESCRIPTION OF THE DRAWING

My new variety of African violet plant is illustrated by the accompanying drawing which shows the form and color characteristics of the plant and its blooms, the color rendition being as nearly true as is reasonably possible to obtain by conventional photographic procedures. The upper view shows details of the blossoms and the manner in which they are borne on the flower stalk and the lower view shows the entire plant in full bloom. The color patches A and B show the true colors of the top and under sides, respectively, of the flower petals.

DESCRIPTION OF THE NEW PLANT

The following is a detailed description of my new variety of African violet plant with color designations according to the Horticultural Colour Chart published by the British Colour Council in collaboration with the Royal Horticultural Society.

*The plant*

Origin: Seedling
Parentage:
- *Seed parent.*—A *Saintpaulia ionantha* of unknown origin
- *Pollen parent.*—Blaues Mäerchen (unpatented)

Classification:
- *Botanic.*—*Saintpaulia ionantha*
- *Commercial.*—African violet Form: Compact potted plant (rosette arrangement)
Height: To 3¼ inches from base to top of flowers
Growth: Condensed and vigorous, sturdy with tendency to be clumpy
Foliage: Quantity—abundant
- *Size of leaf.*—Up to 2 inches in diameter
- *Shape of leaf.*—Generally cordate with crenate margins

- *Texture.*—Very leathery and tough
- *Aspect.*—Shiny and very tomentose
- *Veins.*—Pinnate and very pronounced on under side. Veins connect at leaf edges.
- *Color.*—Upper side—Ivy Green 0001060/3. Under side—Magnolia Purple 030/1 with Agatha Green 60/3
- *Petioles.*—1¼ to 1½ inches for older leaves

*The bud*

Form: Pear-shaped, rounded just before opening
Size: Fairly small. 3/16 to ¼ inch in diameter and 3/16 inch in depth
Opening: Very slowly (5 weeks from visible bud to opened flower)
Color: When petals unfurl—Victoria Violet 738
Sepals: Hooded over bud for a very short time
- *Forms.*—Sepals stand up and are spear-shaped
- *Color.*—Inside—Sage Green 000861. Outside—Sage Green 000861

Calyx:
- *Shape.*—Splits to star shape with five sepals
- *Size.*—Small compared to petal size
- *Aspect.*—Very tomentose Peduncle:
- *Length.*—1 to 1¾ inches from base to branching. Branches 7/16 to ¾ inch long.
- *Strength.*—Sturdy but flexible
- *Aspect.*—Very tomentose
- *Color.*—Maroon 1030

*The flower*

Blooming habit: Recurrent the year around with a tendency to bloom early
Size of Flower:
- *Medium.*—Varies with age of plant
- *Diameter.*—⅞ to 1¼ inches
- *Depth.*—To ¾ inch Borne: In cluster on each primary peduncle
Shape: Very open cup-shaped when bloom first opens changing to wide open, flatter cup
Petalage: Number of petals—5, 3 noticeably larger than remaining 2
Arrangement: Smypetalous
Form: Rotate and bilaterally symmetrical
Color:
- *Face side.*—Victoria Violet 738
- *Reverse side.*—Victoria Violet 738/3

Texture: Soft and flexible
Appearance: Velvety and smooth—tomentose on reverse or underside
Peduncle: 1 to 1¾ inches from base to branching. Branches—7/16 to ¾ inch long
- *Strength.*—Sturdy and fairly upright
- *Color.*—Maroon 1030

Discoloration after full bloom: Color becomes darker
Effect of weather: Hot environment suppresses flowering and fades flower color, 80% to 90% relative humidity most favorable
Fragrance: None
Lasting quality: 10 to 14 days for full opened flower
Persistance: Blossoms hang on and dry on the stalk

*Reproductive organs*

Stamens:
- *Anthers.*—Arrangement—basifixed; 2 in number, each 1/16 inch long and composed of 2 anther cells
- *Filaments.*—Single filament ⅛ inch long. Color—Victoria Violet 738 surrounding Citron. Green 763/3
- *Pollen.*—Color—White Pistils: One in number, 7/16 inch long
Stigmas: Color—Victoria Violet 738
Style: 1/4 inch long and Victoria White 738 in color
Ovaries: Superior and tomentose, yellow color appears below ovary The principal advantages of this new variety of African violet plant are to be found in the distinctive form of the wide open flower which has more depth than most varieties and the upstanding display of the flowers which an unusually dark violet color. The plant grows vigorously with heavy and uniform flowering and produces abundant foliage, although plantlet production from cut leaf propagation is low compared to other varieties.

I claim:

1. A new variety of African violet plant, substantially as herein shown and described, characterized by the deep violet color and open-cup shape of its flowers, its year around blooming habit and the upstanding display of the blooms.

No references cited.

ROBERT E. BAGWILL, Primary Examiner